United States Patent
Kay et al.

(10) Patent No.: US 8,257,406 B2
(45) Date of Patent: Sep. 4, 2012

(54) ORTHOPEDIC PLATE FOR USE ON A SINGLE RAY IN THE MIDFOOT

(75) Inventors: David B. Kay, Akron, OH (US); Dustin Ducharme, Stow, OH (US); Andrew J. Leither, Akron, OH (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 504 days.

(21) Appl. No.: 12/378,541

(22) Filed: Feb. 17, 2009

(65) Prior Publication Data
US 2009/0210013 A1  Aug. 20, 2009

Related U.S. Application Data

(60) Provisional application No. 61/066,235, filed on Feb. 19, 2008.

(51) Int. Cl.
*A61B 17/80* (2006.01)

(52) U.S. Cl. .......................... 606/286; 606/280

(58) Field of Classification Search .......... 606/280–299, 606/70, 71
See application file for complete search history.

(56) References Cited

U.S. PATENT DOCUMENTS

| | | | |
|---|---|---|---|
| 4,219,015 A * | 8/1980 | Steinemann | 606/280 |
| 4,493,317 A | 1/1985 | Klaue | |
| 5,601,553 A * | 2/1997 | Trebing et al. | 606/86 B |
| D449,692 S | 10/2001 | Michelson | |
| 6,565,571 B1 | 5/2003 | Jackowski et al. | |
| 6,576,018 B1 | 6/2003 | Holt | |
| 6,623,486 B1 * | 9/2003 | Weaver et al. | 606/281 |
| 7,052,499 B2 | 5/2006 | Steger et al. | |
| 7,108,697 B2 | 9/2006 | Mingozzi et al. | |
| 7,189,237 B2 | 3/2007 | Huebner | |
| 2005/0059971 A1 * | 3/2005 | Michelson | 606/69 |
| 2006/0015102 A1 | 1/2006 | Toullec et al. | |
| 2006/0081553 A1 | 4/2006 | Patterson et al. | |
| 2006/0106387 A1 | 5/2006 | Fanger et al. | |
| 2006/0173459 A1 * | 8/2006 | Kay et al. | 606/69 |

(Continued)

FOREIGN PATENT DOCUMENTS

JP    20030102744    4/2003

(Continued)

OTHER PUBLICATIONS

Diamond Carpal Fusion Plate Surgical Plate by Small Bone Innovations (13 pages).

(Continued)

*Primary Examiner* — Thomas Barrett
*Assistant Examiner* — Melissa A Golob
(74) *Attorney, Agent, or Firm* — Hudak, Shrunk & Farine Co. LPA

(57) ABSTRACT

An orthopedic plate is specifically configured for implantation at the mid-foot and can be used for a variety of indications. The plate has a set of tabs comprising one longer tab and one shorter tab opposing each other along the length of the plate. In each set of tabs, one tab includes a compression slot that extends in a direction toward a screw hole in the opposing tab.

11 Claims, 1 Drawing Sheet

U.S. PATENT DOCUMENTS

| | | | |
|---|---|---|---|
| 2006/0235396 A1 | 10/2006 | Sanders et al. | |
| 2006/0235397 A1 | 10/2006 | Sanders et al. | |
| 2006/0241592 A1 | 10/2006 | Myerson et al. | |
| 2006/0241607 A1 | 10/2006 | Myerson et al. | |
| 2006/0241608 A1 | 10/2006 | Myerson et al. | |
| 2007/0016205 A1 | 1/2007 | Beutter et al. | |
| 2007/0073298 A1 | 3/2007 | Beutter et al. | |
| 2007/0083204 A1 | 4/2007 | Sidebotham | |
| 2007/0233114 A1* | 10/2007 | Bouman | 606/69 |

FOREIGN PATENT DOCUMENTS

| | | |
|---|---|---|
| JP | 20060280951 | 10/2006 |

OTHER PUBLICATIONS

VariAx Foot Locking Plate System by Stryker dated 2009 (23 pages).
The corresponding International Search Report and Written Opinion dated Mar. 27, 2009.
Techtonix Surgical Protocal (1 page).
Foot Reconstructive and Trauma Surgery—Internal and External Fixation Systems May 29, 2008 (pp. 2-12).
New Trauma Products from AO Development, Jun. 2006 (pp. 2&3).
A Straight Answer for Kids, Jan. 2007 (4 pages).

* cited by examiner

ORTHOPEDIC PLATE FOR USE ON A SINGLE RAY IN THE MIDFOOT

CROSS-REFERENCE

This is a U.S. patent application of U.S. Provisional Application No. 61/066,235 filed on Feb. 19, 2008 for ORTHOPEDIC PLATE FOR USE ON A SINGLE RAY IN THE MIDFOOT which is hereby fully incorporated by reference.

FIELD OF THE INVENTION

The present invention relates to an orthopedic plate which is configured for the fixation of a bone or bones of the midfoot including, for example, stabilization of a fracture, dislocation or reconstruction of a deformity.

BACKGROUND OF THE INVENTION

Together the foot and ankle have over 25 bones and 33 joints along with more than 100 named muscles, tendons, and ligaments and a network of blood vessels, nerves, all residing beneath a relatively slim covering of soft tissue and skin. Structurally, the foot has three main anatomical regions: the forefoot, the midfoot, and the hindfoot. These parts work together with the ankle, to provide the body with support, balance, and mobility. A structural flaw or malfunction in any one part can result in the development of problems, which are manifested in other areas of the body.

The forefoot includes the five toes (which are also known as the "phalanges") and their connecting long bones (or "metatarsals"). Several small bones together comprise a phalanx or toe. Four of the five toes have three phalanx bones respectively connected by two joints. The big toe (or "hallux") has two phalanx bones distal and proximal with a joint in between called the interphalangeal joint. The big toe articulates with the head of the first metatarsal at the first metatarsophalangeal joint (the "MTP" joint) and there are two tiny, round bones called sesamoids on the plantar side of the metatarsal head. The phalanges are connected to the metatarsals at the ball of the foot. The forefoot balances pressure on the ball of the foot and bears a substantial amount of the body weight.

The bones of the midfoot from medial to lateral are the $1^{st}$ through $3^{rd}$ cuneiform, the cuboid, and the crescent shaped navicular bone posterior to the cuneiforms, which also forms a joint with the talus that forms the basis for the ankle joint at the hinged intersection of the tibia, the fibula, and the foot The five tarsal bones of the midfoot act together form a lateral arch and a longitudinal arch which help to absorb shock. The plantar fascia (arch ligament) underlays the bones of the midfoot and along with muscles, forms a connection between the forefoot and the hindfoot. The toes and their associated midfoot bones form the first through fifth rays beginning with the great toe as the first ray.

The hindfoot is composed of three joints (subtalar, calcaneocuboid & talonavicular) and links the midfoot to the ankle. The heel bone (or "calcaneus") projects posteriorly to the talus and forms a lever arm to activate the hinged action of the foot so as to allow propulsion of the entire body from this joint. The calcaneus is joined to the talus at the subtalar joint.

The mid-foot is often the subject of trauma such as results from falls, vehicle crashes and dropped objects. These accidents often result in severe fractures and/or dislocations. A common midfoot fracture is the Lisfranc injury which was identified by a French doctor in the Napoleonic Wars. It commonly occurred when a cavalier fell from his horse with his foot caught in his stirrup and resulted in the fracture and dislocation of multiple bones of the midfoot. A Lisfranc injury has come to indicate an injury to the normal alignment of the cuneiforms and metatarsal joints with the loss of their normal spatial relationships. These types of injuries may occur from dropping a heavy object on the top of the foot or stepping on an uneven surface and falling with the foot in a twisted position. These fractures also occur in athletes when the foot is bound to an article of sports equipment such as skis or snowboards or when the foot is subject to simultaneous impact and rotation, such as skating or ballet jumps or soccer.

A common Lisfranc injury occurs at the joint primarily involving the 1st and 2nd metatarsals and the medial cuneiform. Normal alignment of the joints is lost if the ligaments are disrupted and the bones separate between the medial and mid-cuneiforms or between the 1st, 2nd metatarsal and the medial cuneiform. Failure to treat such an injury may result in joint degeneration and subsequent damage to the adjacent nerves and blood vessels.

Typical surgical treatment of the midfoot re-establishes the normal anatomy of the mid-foot while the fractured bones mend. In some cases, fusion of the joint between the first and second metatarsals and the middle and/or internal cuneiforms may be necessary, for example, where arthritis arises in patients with a prior Lisfranc or similar injury. One current surgical treatment of this injury requires that pins, wires and/or screws be inserted to stabilize the bones and joints and hold them in place until healing is complete. For example, a pin or screw may be introduced medially into the internal cuneiform and through the base of the second metatarsal bone. While the use of k-wires, pins, and screws may provide acceptable results for younger and more plastic patients, these methods of fixation are not always satisfactory.

SUMMARY OF THE INVENTION

In accordance with the present invention an orthopedic plate is provided that is a handy and elegant little plate that can be used in place of a compression staple with better pull-out values, improved compression, and less harm to the bone in which it is used. The invention can be used in a wide variety of indications including for example, lapidus bunionenctomy, calcaneolocuboid fusion, talonavicular fusion, MTP fusion, cuboid fracture, metarsocunieform fusion, chevron osteotomy, Naviculocuneioform fusion, Dwyer osteotomy, cotton osteotomy, isolated TMT fusion, Navicular fracture, Evans osteotomy and the previously mentioned Lisfranc fracture. The present invention is further specifically configured for implantation at the mid-foot and more specifically is configured for use in a single ray The plate has a dumbbell or peanut shaped, footprint which consists simply of two rounded tabs along the longitudinal axis of the plate with a narrowed waist section between the tabs. The longer of the two tabs includes a compression slot that extends in a direction and causes compression toward a locking screw hole in the opposing tab. The plate is radiused along the bottom surface along the longitudinal axis of the plate so that the plate forms a section of a cylinder, which is bilaterally symmetrical with respect to a plane passing through the longitudinal axis.

DETAILED DESCRIPTION OF THE INVENTION

Figure 1:
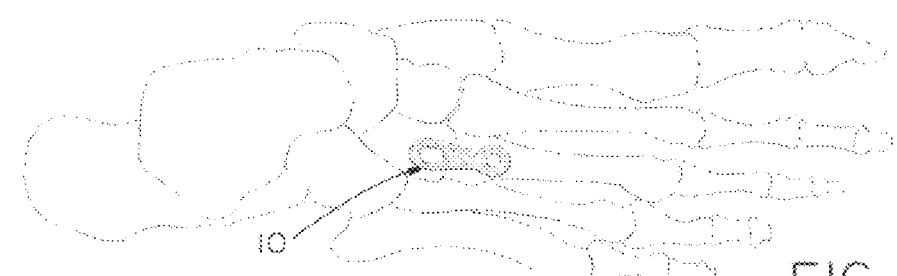
FIG. 1 is a dorsal view of a mid-foot with an orthopedic plate in accordance with the invention is positioned for the third ray.

FIG. 1 shows a skeletal version of a foot from the top (i.e. the dorsal view) with the midfoot plate 10 of the present invention in place between the junction of the third metatarsal and the third cuneiform (i.e. the lateral cuneiform). Thus. FIG. 1 illustrates the plate used in fixation of the bones of the third ray or 3nd TMT (tarso-metatarsal) joint. The plate can also be used for fixation of the first and second ray, that is, for fixation of the 1st TMT joint (1st metatarsal to medial cuneiform) and 2nd TMT joint (2nd Metatarsal to middle or intermediate cuneiform). Similarly, it can be used for fixation of the joints of the other rays, for example where a surgical staple might currently be used.

Figure 2:
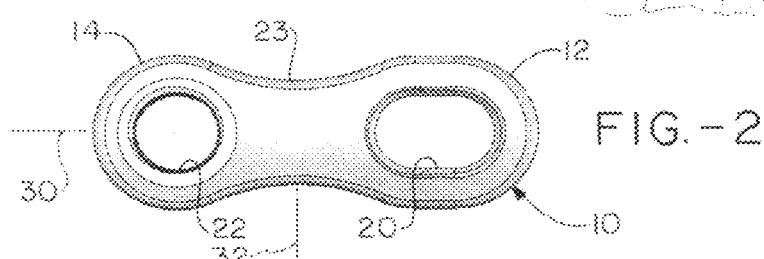
FIG. 2 is a top view of the orthopedic plate of FIG. 1.

As viewed from the top in FIG. 2, it can be seen that the plate 10 has two opposing tabs comprising a longer tab 12 and a second shorter tab 14 aligned along the longitudinal axis of the plate. The longer tab 12 includes a compression slot 20, and the other 14 of the pair of tabs includes a screw hole 22 (which preferably includes locking means such as internal threads or a variable locking mechanism, so as to form a locking interface between the plate and the respective bone or bone fragment by means of the rigid fastening of the screw in the screw hole in the plate.) The compression slot is configured so as to cause compression along the longitudinal axis 30 of the plate in the direction of the locking screw hole. The plate includes incurvatures 23 between the tabs to form a waist section which minimizes the material used and maximizes the fit of the plate, as well as allowing additional contouring of the plate in this area, should it be desired.

Figure 3:
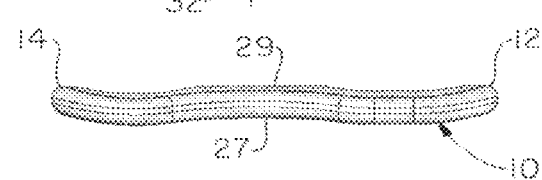
FIG. 3 is a side view of the plate shown in FIG. 2.
Figure 4:
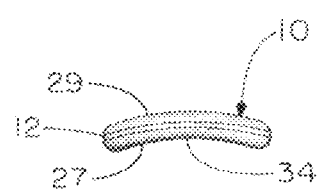
FIG. 4 is an end view of the plate shown in FIG. 3.
Figure 5:
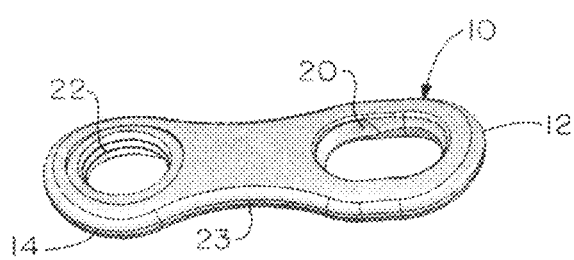
FIG. 5 is a top perspective of the plate shown in FIG. 2.
Figure 6:
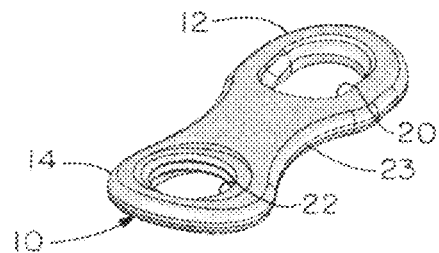
FIG. 6 is a end perspective of the plate shown in FIG. 2.
Figure 7:
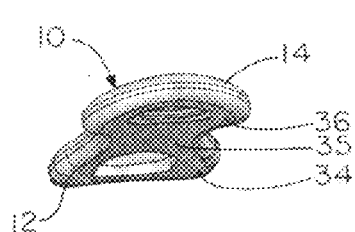
FIG. 7 is a bottom perspective of the plate shown in FIG. 2.
Figure 8:
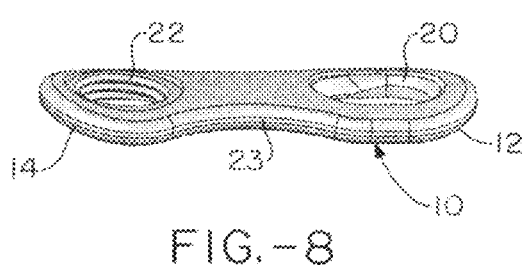
FIG. 8 is a side perspective of the plate shown in FIG. 2.

FIGS. 3 and 4 illustrate the edge on views of the plate in along a first length and along the second shorter length which is perpendicular to the first length. As can be seen the plate has a generally uniform thickness between the inward surface 27 which opposes and optimally, but not necessarily engages the bones, and the outward surface 29. In addition, the inward surface 27 of the plate 10 includes a generally uniform radius of curvature 34 along the longitudinal axis. Thus, the plate has the shape of a segment of a cylinder which maximizes the ability to place the plate as desired without the need for additional pre-surgical contouring, although the plate thickness allows for bending if necessary The screws useful with the plate of the present invention are self-starting, self-tapping screws including the option of partial or full cannulation. The screws include a cutting end having multiple flutes, and preferably 2 or 3 flutes about a conical recess. The screws further include a partial taper of the inner diameter in the proximal end over the first several thread turns, for example over 2-8, and preferably over 3-5 turns in order to increase the fatigue life of the screw as well as providing potential physiological advantages in use. The screws further include a torque driving recess. The screws have a threaded distal end and a head including a torque driving recess. The head of the locking screw includes locking means, such as a variable locking mechanism, which could be a bushing that mates with the screw head so as to lock the screw relative to the plate at a desired angle, or could include external screw threads that mate with internal threads in the locking screw hole at a pre-selected angle, in this instance, the screw axis is perpendicular to the longitudinal axis of the plate. The screw used in the compression slot has a rounded rear shoulder (such as a hemisphere, or a torroid) which mates with the concavely rounded groove of the compression slot so as to maximize surface contact between the screw head and the inclined geometry of the compression slot. The lateral edge of the compression slot further includes an inclined shoulder that slopes downward toward the bone-contacting surface of the plate and which is engaged by the screw head to cause the translation of the screw and attached bone fragment along the long axis of the slot and towards the locking hole.

The plate is formed of a biocompatible material, and preferably a metal such as surgical grade stainless steel, titanium or a titanium alloy. Preferably, the plate has a thickness of between about 1.0 and 2.0 millimeters, more preferably between about 1.25 and 1.75 millimeters, and most preferably between about 1.4 and 1.6 millimeters. The plate includes a continuous outer edge 40 which is defined between the top and the bottom surface.

In addition, the plate 10 can include a small through hole sized to receive a K-wire or other similar guide wire.

During the surgery the joints are first prepped which may include de-articulation between the bones to be fused. The proper length plate is selected and as necessary, the plate is bent to contour to the bone surface. The plate is placed and held in place using olive wires (thru compression slot and into the bone). The plate is located such that all of the screws are aimed into the targeted bones and away from the joint, fracture, or bone interface. A pilot hole is drilled, for example using a drill guide such as a guide including keyway guides (i.e. lobes) that interlock with corresponding keyway openings in the locking screw hole. The locking screw is tightly screwed into the bone. The olive wire is removed if used, and a pilot hole is drilled at the end of the compression slot farthest away from the fusion or fracture and locking hole. A non-locking screw is inserted into the pilot hole and tightened. As the screw is tightened in the compression slot, it will drive compression toward the fusion site and locking hole. The plate allows for up to 1.5 millimeters of compression. The plate is viewed radiographically, and the soft tissues are closed in the usual manner.

While in accordance with the patent statutes the best mode and preferred embodiment have been set forth, the scope of the invention is not limited thereto, but rather by the scope of the attached claims.

What is claimed is:

1. A plate system for use in associated bone comprising a locking screw, a non-locking screw having a head, and a plate having a top surface and a bone facing surface, the plate consisting essentially of a peanut-shaped profile having a locking hole and a compression slot, the profile comprising a first rounded tab terminating in a portion of a circle and a second rounded tab terminating in a portion of a circle and the first rounded tab and the second rounded tab being aligned along a medial longitudinal axis and joined by a middle section having incurvatures to form a curving waist section wherein the middle section has a width perpendicular to the medial longitudinal axis which is smaller than the width of either the first rounded tab or the second rounded tab, the first rounded tab including the locking hole having internal threads for a locking screw, the locking hole having a midline, and the second rounded tab including a compression slot having a long axis, the compression slot defining a first lateral edge and a second lateral edge which each include an inclined shoulder that slopes downward toward the bone facing surface of the plate parallel to the long axis of the compression slot, the midline of the locking hole and the long axis of the compression slot being aligned along the medial longitudinal axis of the plate, and the inclined shoulder of the compression slot being engaged by the non-locking screw head to cause the translation of the non-locking screw along the long axis of the slot and towards the locking hole to cause compression in the direction of the long axis in the associated bone toward the locking hole in use, and the plate optionally including at least one other hole for a k wire.

2. A plate system as set forth in claim 1 wherein the plate has a generally uniform thickness between the top surface and the bone facing surface.

3. A plate system as set forth in claim 2 wherein the bone facing surface includes a radius of curvature along the longitudinal axis.

4. A plate system as set forth in claim 3 wherein the plate comprises a portion of a cylinder.

5. A plate system as set forth in claim 1 wherein the locking screw includes a variable locking mechanism.

6. A plate system for use in associated bone comprising a locking screw having distal threads and a head having external threads, a non-locking screw having distal threads and a head having a rounded surface, and a plate being a section of a cylinder and having a medial longitudinal axis and a transverse medial axis and having a profile with bilateral mirror symmetry about the medial longitudinal axis, the plate consisting of a first end having a locking hole and a second end having a compression slot, the first end being a first tab having a terminal circular portion having a first diameter and a second end being a second tab having a terminal circular portion having a second diameter which may be the same or different than the first diameter, the first and second end being aligned along the medial longitudinal axis of the plate and joined by a middle section formed by incurvatures to form a curving waist section which has a width in the direction perpendicular to the longitudinal axis, the first tab including the locking hole for a locking screw having a midline, and the compression slot being an obround slot having a long axis and the compression slot defining a first lateral edge and a second lateral edge which each include an inclined shoulder that slopes downward toward the bone facing surface of the plate and parallel to the long axis of the compression slot, the midline of the locking hole and the long axis of the compression slot being aligned along the medial longitudinal axis of the plate and the inclined shoulder of the compression slot being engageable by the non-locking screw head to cause the translation of the non-locking screw along the long axis of the slot and toward the locking hole to cause compression in the direction of the long axis in the associated bone toward the locking hole in use, and optionally including a hole for a k-wire.

7. A plate system as set forth in claim 6 wherein the system further includes a drill guide which interacts with the locking hole to allow a pilot hole to be drilled in the associated bone at a desired angle.

8. A plate system as set forth in claim 7 wherein the drill guide includes guides and the locking hole includes grooves which capture the guides to fix the angle of the drill guide.

9. A method of fusing bones, comprising:
surgically accessing a bone,
selecting a plate which is a section of a cylinder and having a profile with bilateral mirror symmetry along a medial longitudinal axis of the plate, the profile being a peanut-shape comprising a first end which is a tab having a terminal circular portion having a first diameter and a second end which is a tab having a terminal circular portion having a second diameter which may be the same or different than the first diameter, the first and second end being aligned along a medial longitudinal axis of the plate and joined by a middle section formed by incurvatures to form a curving waist section which has a width in the direction perpendicular to the longitudinal axis, the width being smaller than the first diameter and the second diameter, the first tab including a locking hole having a midline for a locking screw, and the second tab including an obround compression slot, the compression slot having a long axis and the compression slot defining a first lateral edge and a second lateral edge which each include an inclined shoulder that slopes downward toward the bone facing surface of the plate and parallel to the long axis of the compression slot, the midline of the locking hole and the long axis of the compression slot being aligned along the medial longitudinal axis of the plate, the midline of the locking hole and the long axis of the compression slot being aligned along the longitudinal axis, the plate consisting of the peanut shaped profile having the locking hole and the compression hole, and optionally a hole for a k-wire;
fixing a locking screw in the locking hole;
fixing a non-locking screw in the compression slot so that the inclined shoulder of the compression slot is engaged by the non-locking screw head to cause the translation of the non-locking screw along the long axis of the slot and towards the locking hole to cause compression in the associated bone along the long axis of the slot and toward the locking hole.

10. A method of fusing bones as set forth in claim 9 wherein a drill guide is used to drill a pilot hole for the non-locking screw.

11. A method of fusing bones as set forth in claim 10 wherein a drill guide is used to drill a pilot hole for the locking screw.

* * * * *